United States Patent
Panerai et al.

(10) Patent No.: US 6,255,283 B1
(45) Date of Patent: *Jul. 3, 2001

(54) USE OF PROTEINS EXTRACTABLE FROM ANIMAL ORGANS FOR THE PREPARATION OF MEDICAMENTS FOR THE TREATMENT OF PATHOLOGICAL CONDITIONS CHARACTERIZED BY HYPERPRODUCTION OF TUMOR NECROSIS FACTOR (TNF)

(75) Inventors: Alberto Panerai; Pier Luigi Meroni; Alberto Bartorelli, all of Milan (IT)

(73) Assignee: Zetesis S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/381,737

(22) PCT Filed: Mar. 16, 1998

(86) PCT No.: PCT/EP98/01516

§ 371 Date: Oct. 19, 1999

§ 102(e) Date: Oct. 19, 1999

(87) PCT Pub. No.: WO98/42366

PCT Pub. Date: Oct. 1, 1998

(30) Foreign Application Priority Data

Mar. 25, 1997 (IT) .............................................. MI97A0694

(51) Int. Cl.⁷ .................................................... A61K 38/17
(52) U.S. Cl. ............................... 514/12; 514/21; 530/350
(58) Field of Search ................................... 530/350, 395; 514/2, 8, 12, 21

(56) References Cited

U.S. PATENT DOCUMENTS 5,997,873 * 12/1999 Srivastava .......................... 424/193.1
6,007,821 * 12/1999 Srivastava et al. ............... 424/193.1

FOREIGN PATENT DOCUMENTS

| 2 251 186 | 7/1992 | (GB) . |
| 93/18146 * | 9/1993 | (WO) . |
| 96 02567 | 2/1996 | (WO) . |
| 96 10039 | 4/1996 | (WO) . |
| 98 11909 | 3/1998 | (WO) . |

OTHER PUBLICATIONS

Chemical Abstracts, vol. 119, No. 7, Aug. 16, 1993, Abstract No. 65937, XP002075248, F. Levy–Favatier et al, "Characterization, purification and cDNA cloning of a rat perchloric–acid–soluble 23 kDa protein etc."

* cited by examiner

Primary Examiner—Jeffrey E. Russel
(74) Attorney, Agent, or Firm—Birch, Stewart, Kolasch & Birch, LLP

(57) ABSTRACT

Proteins extractable with perchloric acid from mammal liver, in particular from goat liver, are capable of lowering blood levels of Tumor Necrosis Factor (TNF) and can be used for the treatment of multiple sclerosis, rheumatoid arthritis, septic shock and other pathologies characterized by TNF hyperproduction.

3 Claims, No Drawings

SEQUENCE LISTING

<160> NUMBER OF SEQ ID NOS: 1

<210> SEQ ID NO 1
<211> LENGTH: 137
<212> TYPE: PRT
<213> ORGANISM: mammalian

<400> SEQUENCE: 1

```
Met Ser Glu Asn Ser Glu Glu Pro Val Gly Glu Ala Lys Ala Pro Ala
 1               5                  10                  15

Ala Ile Gly Pro Tyr Ser Gln Ala Val Leu Val Asp Arg Thr Ile Tyr
                20                  25                  30

Ile Ser Gly Gln Leu Gly Met Asp Pro Ala Ser Gly Gln Leu Val Pro
            35                  40                  45

Gly Gly Val Val Glu Glu Ala Lys Gln Ala Leu Thr Asn Ile Gly Glu
        50                  55                  60

Ile Leu Lys Ala Ala Gly Cys Asp Phe Thr Asn Val Val Lys Ala Thr
65                  70                  75                  80

Val Leu Leu Ala Asp Ile Asn Asp Phe Ser Ala Val Asn Asp Val Tyr
                85                  90                  95

Lys Gln Tyr Phe Gln Ser Ser Phe Pro Ala Arg Ala Ala Tyr Gln Val
                100                 105                 110

Ala Ala Leu Pro Lys Gly Gly Arg Val Glu Ile Glu Ala Ile Ala Val
            115                 120                 125

Gln Gly Pro Leu Thr Thr Ala Ser Val
        130                 135
```

USE OF PROTEINS EXTRACTABLE FROM ANIMAL ORGANS FOR THE PREPARATION OF MEDICAMENTS FOR THE TREATMENT OF PATHOLOGICAL CONDITIONS CHARACTERIZED BY HYPERPRODUCTION OF TUMOR NECROSIS FACTOR (TNF)

The present invention relates to the use of proteins extractable from animal organs for the preparation of medicaments for the treatment of pathological conditions characterized by hyperproduction of Tumor Necrosis Factor (TNF).

TNF, also known as cachectin, is a proinflammatory cytokine playing an important role in starting, together with IL-1, the cascade of other cytokines and factors which trigger the immune response in infections and in cancer. This response is paramount for a complete resolution of infections and metastatic processes, but it can occur in an uncontrolled way, thus causing damage to the host. TNF hyperproduction is considered to be involved in a number of pathological conditions, such as septic shock, tumor cachexia, autoimmune diseases (rheumatoid arthritis, multiple sclerosis), meningococcal septicemia, Crohn's disease, etc.

WO 92/10197 disclosed protein fractions extractable with perchloric acid from organs of mammals, and their use as anticancer agents. Within these fractions, three main components could be identified, having molecular weights of 50, 14 and 10 KDa on gel electrophoresis. Hereinafter, the purified extract containing these three components will be referred to as UK 101. The sequence of the 14 KDa component, which is the main, if not the only protein, responsible for the described activities, is reported in WO 96/02567 and it has turned out to be related to that described by other authors (Levy-Favatier, Eur. Biochem. 1903, 212 (3) 665–73) who have assumed that the novel identified sequences belong to the family of the proteins known as chaperonins, to which the HSPs (Heat Shock Proteins) themselves belong.

The proteins described in WO 92/10197 and those of WO 96/02567 (hereinafter referred to as UK 114) show properties not previously observed in chaperonins or analogous proteins. Now it has been found, in particular, that said proteins are capable of significantly lowering TNF blood levels and therefore they can be used for the treatment of pathological conditions characterized by hyperproduction of TNF.

The invention relates particularly to the use of the purified protein UK 114.

Moreover the invention comprises the use of proteins showing high homology to UK 114, of at least 80%, especially of 90% or more.

The activity of the proteins UK 101 and UK 114 has been demonstrated in vitro, on mononuclear leukocytes from peripheral blood and in vivo, by evaluating the effect of the administration of UK 101 on the production by mouse splenocytes as reported hereinafter.

In Vitro Tests

Mononuclear leukocytes from peripheral blood (PBMC), at a concentration of 1 million/ml, were stimulated in vitro with lipopolysaccharide (100/ ng/ml), for 4 hour in the absence or in the presence of UK 114 (1 $\mu$g/ml and 10 $\mu$g/ml).

TNF Levels Were Measured by ELISA

Results

TNF production by PBMC was inhibited by the addition of UK 114 in vitro.

The decrease was by 90% with a 1 $\mu$g/ml dose of UK 114 and by 70% with a 10 $\mu$g/ml dose of UK 114.

In Vivo Tests

Treatment

Mice were treated with 100 $\mu$g/mouse of UK 101 on alternate days for 15 days (7 injections).

TNF has been measured 48 hours after the first injection and 48 hours after the last administration.

Preparation of the Cells and TNF Measurements

Splenocytes ($4\times10^6$ cells/ml) were incubated in the presence of 10 $\mu$g/ml of the polyclonal mitogen Concanavalin-A (With-A), for 48 hours, at 37°C., 5% $CO_2$.

The amount of produced TNF released into the supernatant has been evaluated using an immunoenzymatic method (ELISA).

Results

Treatment with UK 101 significantly decreased TNF production by mouse splenocytes. The effect is evident 48 hours after the first administration and it is still present even 48 hours after the seventh administration.

| | TNF, pg/ml | |
|---|---|---|
| | physiological saline | UK-101 |
| 48 hours after the 1st administration | 387 ± 72 | 247 ± 30° |
| 48 hours after the 7th administration | 366 ± 46 | 264 ± 76,1° |

° = p value

Therefore, UK 101 and UK 114 are capable of modifying the course of, or preventing, pathological conditions characterized by TNF hyperproduction, such as multiple sclerosis, rheumatoid arthritis, tumor forms, septic shock, Crohn's disease, etc.

The proteins of the invention can be administered by means of suitable formulations, preferably injectable forms.

The procedure of administration (doses, frequency of administration, etc.) will be determined according to the circumstances, depending on a number of factors such as the condition of the patient, stage of the disease. Nevertheless a daily dosage ranging from 1 to 100 mg will be suitable.

TABLE (SEQ ID NO: 1)

```
Met Ser Glu Asn Ser Glu Glu Pro Val Gly Glu Ala
1               5                   10
Lys Ala Pro Ala Ala Ile Gly Pro Tyr Ser Gln Ala
        15                  20
Val Leu Val Asp Arg Thr Ile Tyr Ile Ser Gly Gln
25                  30                      35
Asp Ile Asn Asp Phe Ser Ala Val Asn Asp Val Tyr Lys
Gln
Leu Gly Met Asp Pro Ala Ser Gly Gln Leu Val Pro
            40                      45
Gly Gly Val Val Glu Glu Ala Lys Gln Ala Leu Thr
    50                  55                      60
Asn Ile Gly Glu Ile Leu Lys Ala Ala Gly Cys Asp
                65                      70
Phe Thr ASn Val Val Lys Ala Thr Val Leu Leu Ala
        75                      80
Asp Ile Asn Asp Phe Ser Ala Val Asn Asp Val Tyr
85                  90                      95
Lys Gln Tyr Phe Gln Ser Ser Phe Pro Ala Arg Ala
            100                     105
```

TABLE-continued (SEQ ID NO: 1)

| | | | | | | | | | |
|---|---|---|---|---|---|---|---|---|---|
| Ala | Tyr | Gln | Val | Ala | Ala | Leu | Pro | Lys | Gly | Gly | Arg |
| | 110 | | | | | 115 | | | | | 120 |
| Val | Glu | Ile | Glu | Ala | Ile | Ala | Val | Gln | Gly | Pro | Leu |
| | | | | 125 | | | | | | 130 | |
| Thr | Thr | Ala | Ser | Val | | | | | | | |
| | | | | 135 | | | | | | | |

What is claimed is:

1. A method for treatment of pathologies characterized by TNF hyperproduction, comprising administering to an animal in need of such treatment a treatment-effective amount of a protein having the sequence of SEQ ID NO:1 or a protein having a homology of at least 80% to a protein having the sequence of SEQ ID NO:1.

2. The method according to claim 1, wherein the protein has the sequence of SEQ ID NO:1.

3. A method for treatment of pathologies characterized by TNF hyperproduction, comprising administering to an animal in need of such treatment a treatment-effective amount of a protein extracted with perchloric acid from mammalian liver.

* * * * *